United States Patent
Chan et al.

(10) Patent No.: US 6,719,888 B1
(45) Date of Patent: Apr. 13, 2004

(54) REFERENCE ELECTRODE ASSEMBLY

(75) Inventors: Andy D. C. Chan, Franklin, MA (US); Joseph S. Foos, Needham, MA (US); James E. Rasmussen, Plainville, MA (US); Richard L. Schulkind, Sharon, MA (US); John A. Zalenski, Mendon, MA (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 08/921,103

(22) Filed: Aug. 29, 1997

Related U.S. Application Data (63) Continuation-in-part of application No. 08/552,833, filed on Nov. 3, 1995, now abandoned.

(51) Int. Cl.[7] .......................................... G01N 27/401
(52) U.S. Cl. ..................................... 204/435; 204/402
(58) Field of Search ................................. 204/435, 402

(56) References Cited

U.S. PATENT DOCUMENTS

| | | | | |
|---|---|---|---|---|
| 2,760,922 A | * | 8/1956 | Williams | 204/435 |
| 2,768,135 A | * | 10/1956 | Adelson | 204/435 |
| 3,455,793 A | * | 7/1969 | Watanabe et al. | 204/435 |
| 3,997,420 A | * | 12/1976 | Buzza | 204/415 |
| 4,166,021 A | | 8/1979 | Ross, Jr. et al. | 204/195 |
| 4,250,010 A | | 2/1981 | Kondo et al. | 204/412 |
| 4,592,823 A | * | 6/1986 | Gregory | 204/435 |
| 4,592,824 A | | 6/1986 | Smith et al. | 204/416 |
| 4,714,527 A | * | 12/1987 | Hofmeier et al. | 204/435 |
| 4,906,348 A | * | 3/1990 | Taichi et al. | 204/435 |
| 4,933,048 A | | 6/1990 | Lauks | 204/1.11 |
| 5,384,031 A | | 1/1995 | Anderson et al. | 204/435 |
| 5,397,452 A | | 3/1995 | Buck et al. | 204/435 |
| 5,441,625 A | * | 8/1995 | Ritter et al. | 204/435 |

FOREIGN PATENT DOCUMENTS

| | | |
|---|---|---|
| EP | 201712 | 11/1986 |
| EP | 388017 | 9/1990 |
| EP | 772041 | 5/1997 |
| JP | 57-53648 | 7/1982 |
| WO | 83/03005 | 9/1983 |

OTHER PUBLICATIONS

Covington, A. K. et al., "Improvements in the Precision of pH Measurements", *Analytica Chimica Acta*, 169 (1985) month unavailable p. 221–229.

Dohner, René et al., "Reference Electrode with Free–Flowing Free–Diffusion Liquid Junction", *Anal. Chem.*, 58 (1986) month unavailable p. 2585–2589.

Harbinson, Terence R. et al., "Performance of Flowing and Quiescent Free–Diffusion Junctions in Potentiometric Measurements at Low Ionic Strengths", *Anal. Chem.*, 59 (1987) month unavailable p. 2450–2456.

(List continued on next page.)

*Primary Examiner*—T. Tung
(74) *Attorney, Agent, or Firm*—Weingarten, Schurgin, Gagnebin & Lebovici LLP (57) ABSTRACT

A reference electrode assembly having a constrained-diffusion liquid junction between a liquid junction solution and a sample solution having separate flow paths, said assembly comprising a flow cell having attached thereto a constraint comprising a region of porous material permeable to water and salts; a remote reservoir for holding said liquid junction solution; a means for moving said liquid junction solution from said reservoir to said constraint; and a reference contact region is provided. This unique configuration provides a reference electrode device of the constrained-diffusion liquid junction type useful in pH and/or ion-selective electrode (ISE) potentiometric sensors and is particularly suitable for use in a mini-integrated electrochemical analyzer.

1 Claim, 2 Drawing Sheets

OTHER PUBLICATIONS

Payne, R.B., "An Isotonic Potassium Chloride Liquid Junction Minimises the Effects of Ionic Strength, Protein and Haematocrit on Ionised Calcium Measurement", *Ann. Clin. Biochem.*, 25 (1988) month unavailable p. 228–232.

"Operator's Manual 513 pH/Blood Gas Analyzer and Acid Base Calculator", Instrumentation Laboratory, Inc. (1974) month unavailable.

Bates, R.G. "Determination of pH: Theory & Practice" John Wiley & Sons (1973) (pp. 312–317).

Blaedel, W.J. "Flow–Through Electrochemical Cell with Open Liquid Junction", *Analytical Chemistry*, 50/12 (1978) pp. 1722–1724.

Covington, A. K. et al., "Improvements in the Precision of pH Measurements", *Analytica Chimica Acta*, 169 (1985) p. 221–229.

Dohner, René E. et al., "Reference Electrode with Free–Flowing Free–Diffusion Liquid Junction", *Anal. Chem.*, 58 (1986) p. 2585–2589.

Forbes, G.S. "The Solubility of Silver Chloride in Chloride Solutions and the Existence of Complex Argentichloride Ions" *J. American Chemical Society*, vol. 33, 1911 pp. 1937–1946.

Harbinson, Terence R. et al., "Performance of Flowing and Quiescent Free–Diffusion Junctions in Potentiometric Measurements at Low Ionic Strengths", *Anal. Chem.*, 59 (1987) p. 2450–2456.

Ives, David et al., "Reference Electrodes Theory & Practice" Academic Press, 1961, pp. 48–56 and 413–419.

Payne, R.B., "An Isotonic Potassium Chloride Liquid Junction Minimises the Effects of Ionic Strength, Protein and Haematocrit on Ionised Calcium Measurement", *Ann. Clin. Biochem.*, 25 (1988) p. 228–232.

Sawyer, Donald T., et al. "Experimental Electrochemistry for Chemists", John Wiley & Sons (1974) pp. 26–29.

"Operator's Manual 513 pH/Blood Gas Analyzer and Acid Base Calculator", Instrumentation Laboratory, Inc. (1974) .

* cited by examiner

REFERENCE ELECTRODE ASSEMBLY

This application is a continuation-in-part, of application Ser. No. 08/552,833, filed Nov. 3, 1995, now abandoned.

FIELD OF INVENTION

This invention provides a reference electrode device of the constrained-diffusion liquid junction type useful in pH and/or ion-selective electrode (ISE) potentiometric sensors and is particularly suitable for use in a mini-integrated electrochemical analyzer.

BACKGROUND OF INVENTION

Conventional types of reference electrodes have a liquid junction where the sample meets the junction solution. The junction is typically either open or constrained. In an open junction system, the liquid junction operates by free diffusion. In a constrained-diffusion junction system, a region of porous material permeable to water and salts (a membrane, porous plug, frit, or the like) is placed at the site of the liquid junction. The porous material acts as a constraint whereby passage of large molecules (such as protein) and bulk liquid transport is generally hindered.

The liquid junction solution (also commonly referred to as the salt bridge solution) typically contains a solution saturated with a salt (such as an equitransferent salt, including KCl, $KNO_3$) which functions to reduce and maintain constant the interfacial potential which develops across the liquid junction boundary, typically referred to as a liquid junction potential. The difference in liquid junction potentials between the system calibrator and the sample is referred to as the residual liquid junction potential. Typically, the residual liquid junction potential increases as the ionic strength difference between the system calibrator solution and the sample solution increases. The residual liquid junction potential is generally considered to compromise the accuracy of the associated potentiometric sensors and therefore a multi-use reference electrode is typically designed to minimize the residual liquid junction potential for as long as possible, while balancing other design constraints.

In potentiometric systems that are designed with miniaturized working or indicator electrodes (typically pH and/or ion selective electrodes), the necessity of the junction solution makes miniaturization of a reference electrode difficult. Further, for the reference electrode to have a multiple use capability, the liquid junction solution must be present in a volume and concentration sufficient to minimize the residual liquid junction potential over its useful lifetime. This requisite volume particularly complicates miniaturization of constrained diffusion liquid junctions since the volume must typically be maintained close to the constraint to minimize problems associated with excessive ion depletion through the constraint. Another drawback of this type of reference electrode is that it tends to be orientation dependent. During operation, an upright orientation generally must be maintained with the liquid junction solution on top of the constraint in order to maintain contact therebetween. Moreover, in order to minimize errors due to the residual liquid junction potential, the junction solution is generally saturated with the equitransferent salt.

Conventional reference electrodes utilize a reference contact region (also sometimes referred to as electrode elements) immersed in a stagnant portion of the junction solution which contains a constant concentration of the equitransferent salt. The reference contact region is often silver based, consisting of an electrochemically reversible redox electrode couple such as $Ag/Ag^+$ and $Ag/AgCl$. When salt solutions are used with silver based reference contact regions such as $Ag/AgCl$, the $AgCl$ is susceptible to dissolution. In constrained-diffusion type liquid junctions, this dissolution is problematic because it leads to subsequent precipitation of silver salts on the region of porous material constraint, thus leading to undesirable fouling of the constraint, which in turn generally results in an erratic reference electrode performance.

Commonly, because of the above-described fouling problem associated with the use of silver based reference contact regions, barrier membranes have been used to restrict $Ag^+$ ion migration from the reference contact region to the porous material constraint region. The use of a barrier membrane, however, carries with it inconvenience because the first use wet-up of the reference electrode is hindered by the barrier membrane, thus requiring a long soaking time in the junction solution prior to the first use. In addition, any additional component, such as this barrier membrane, tends to complicate miniaturization of the reference electrode.

Another common problem associated with the use of saturated equitransferent salt solutions in constrained-diffusion type of liquid junction reference electrodes is that when the reference electrode is stored and/or used at sub-ambient temperatures, salt crystallization and precipitation may occur between the reference contact region and the region of the porous material at the junction, which in turn leads to erratic reference electrode potentials. An additional problem associated with the use of a saturated equitransferent salt solution is that the saturated solution may contribute to reproducibility and/or accuracy problems with blood samples because of interference caused by precipitation of protein and crenation of red blood cells present in the sample.

Some of the aforementioned drawbacks associated with constrained diffusion liquid junctions are reduced or absent in open (free diffusion) liquid junctions. In this regard, reservoirs for holding of junction solutions have been described for open junction type reference electrodes, where there is no region of porous material to act as a constraint at the junction. For example, A. K. Covington et al. (Anal. Chim. Acta, 1985, 169, pp. 221–229) describe a open junction where the junction solution is moved from a KCl reservoir via a syringe. In this prior art system, the liquid junction is established with each sample, but because this type of system leads to cross-contamination of the liquids upon use, the junction solution must be discarded along with the sample thus leading to increased waste. Moreover, such contamination tends to dictate placement of the reference electrode downstream in the sample path of all working electrodes. This restriction disadvantageously limits flexibility of analyzer configuration.

Moreover, open free-diffusion liquid junction reference electrodes tend to require specific orientations and geometries to provide good reproducible junctions. Reproducibility for open free-diffusion liquid junctions tends to depend on uniform, generally circular junction geometries and a constant orientation. (See, e.g., R. E. Dohner et al. Anal. Chem., 1986, 58, pp. 2585–2589; T. R. Harbinson et al., Anal. Chem., 1987, 59, pp. 2450–2456). The orientation and geometries requirements are particularly limiting when attempting to adapt such a reference electrode to a miniaturized, modular system in which it may be desirable to locate the reference electrode within an array of working electrodes and utilize componentry and dimensions common to those working electrodes. The aforementioned orientation requirement may be particularly troublesome in the event a miniature portable analyzer is desired for use in locations where the electrode array may be utilized in various or unstable orientations, such as may be encountered in the field or in mobile applications such as on board ambulances, ships and/or aircraft.

Thus, although many different reference electrodes are known in the prior art, there is a need to discover alternative reference electrodes for electrochemical analyzers, particularly modular reference electrodes that may be easily adapted for use in a mini-integrated type of analyzer.

SUMMARY OF THE INVENTION

Many of the shortcoming associated with prior art reference electrodes have been overcome with the discovery of a reference electrode assembly of the present invention.

According to the invention, provided is a modular reference electrode assembly adapted for serial integration within an orientation independent array of working electrodes, the working electrodes disposed in a plurality of electrode receiving positions on a support member of an integrated sample analyzer. The reference electrode includes:

a flow cell of modular construction sized and shaped for selective disposition in any of the plurality of electrode receiving positions on the support member, wherein said flow cell is adapted for being serially retained within a sample flow path of the array;

a flow cell of modular construction sized and shaped to interfit between guide members adapted to retain the array of miniaturized working electrodes, wherein the flow cell is adapted for being serially retained within a sample flow path of the array;

a liquid junction disposed within the flow cell;

a remote reservoir for holding a liquid junction solution, the remote reservoir being connected to the flow cell by a liquid junction flow path, the liquid junction flow path being separate from the sample flow path;

a reference contact region in physical contact with the liquid junction solution;

the liquid junction including a constraint having a region of porous material permeable to water and salts, the constraint having a contact portion adapted for contacting the liquid junction solution on one side thereof and a sample solution on an other side thereof;

the constraint adapted to substantially prevent bulk flow of the liquid junction solution therethrough, and to provide an orientation independent, stable liquid junction; and means for moving the liquid junction solution from the reservoir to the constraint and for applying pressure sufficient to maintain the liquid junction solution in contact with the constraint at substantially any orientation of the array of electrodes wherein the flow cell is operable at substantially any orientation.

Also provided is a method for providing a modular, orientation independent reference electrode for a system for potentiometric quantitative analysis. This method includes:

providing a flow cell of modular construction sized and shaped for selective disposition in any of a plurality of electrode receiving positions on a sensor support member adapted to support an array of working electrodes, wherein the flow cell is adapted for being serially retained within a sample flow path of the array;

interfitting the flow cell in series with the array of miniaturized working electrodes;

moving a sample solution through the sample flow path over at least one miniaturized working electrode disposed within the array;

moving the sample solution to the flow cell to form a liquid junction between the sample solution and a liquid junction solution over a porous constraint wherein the sample solution is disposed in contact with one side of the porous constraint and the liquid junction solution is disposed in contact with an other side of the porous constraint, the constraint being adapted to substantially prevent bulk flow of the liquid junction solution therethrough and to provide an orientation independent, stable liquid junction, the liquid junction solution comprising a non-saturated equitransferent salt and being stored in a remote reservoir wherein the liquid junction solution is pumped to the constraint per sample cycle and the liquid junction solution is electrically connected with sensing equipment by a reference contact region in physical contact with the liquid junction solution;

maintaining the liquid junction solution in contact with the constraint with sufficient pressure wherein the flow cell is operable at substantially any orientation of the array of electrodes; and measuring an electric potential developed between the reference contact region and the working electrode.

The inventive reference electrode assembly is particularly useful because it is not orientation and gravity specific. The modular construction enables it to be interchangeably retained at substantially any predetermined location within an array of working electrodes in a configuration similar to that utilized for the working electrodes. Moreover, the present invention may be fabricated as a multiple use reference electrode for use in a mini-integrated electrochemical analyzer having planar miniaturized working electrodes because sufficient liquid junction solution is present for multiple uses without presenting a space problem since the extra liquid junction solution is stored in the reservoir that is remote from where the constrained-diffusion liquid junction is created. Other advantages of preferred embodiments are described herein.

BRIEF DESCRIPTION OF THE DRAWINGS

As described in more detail in the Examples section herein.

DESCRIPTION OF THE PREFERRED EMBODIMENTS

According to the invention, reference electrode 1 has a flow cell or front end 4 where the liquid junction solution meets the sample solution at a junction constrained by a region of porous material or constraint 18 permeable to water and salts. The porous material generally hinders passage of large molecules (such as protein) and bulk liquid transport. Such porous materials have been used extensively in the art as the "constraint" in constrained-diffusion liquid junction reference electrodes and thus are easily recognizable by those skilled in the art and are widely commercially available. Examples of such materials are porous plugs, frits and/or membranes. When selected as the constraint material, porous membranes may be fashioned from such materials as cellophane, cellulose acetate, partially nitrated cellulose polycarbonate, combinations thereof, and so on. Particularly preferred, because of ease of use, cost and availability, is a cellophane membrane.

Flow cell 4 may be fashioned from any suitable material conducive to the overall design of analyzer 1 such that the flow cell material is capable of attachment to the constraint material, as well recognized by those skilled in the art. If a reference contact region 13 is configured as a part of the flow cell, then the material selected should be nonconductive. If the reference contact region of the reference electrode assembly is not a portion of the flow cell, then the material selected may be conductive, if desired.

Attaching the constraint region of porous material to the flow cell where the junction is formed may be accomplished by any number of methods within the skill of one acquainted with the art, including for example, bonding or attaching with welding, adhesives, mechanical compression and the like. The attachment should be secure enough to substantially prevent regions of dead volume in the junction solution. Preferably a hermetic seal is formed between flow cell 4 and constraint 18. The area of the porous material exposed to the sample and/or the junction solution may vary, spanning from the entire flow cell to only a small portion of the flow cell, depending upon the specifications of the analyzer design, and so on. Flow cell 4 can optionally be designed such that the porous material covers a distinct chamber or chamber region 19 of the flow cell, where the constraint covers the chamber region and the liquid junction is formed over the chamber region.

A remote reservoir 10 of the invention functions as a storage unit for excess junction solution. According to the invention, the reservoir is external to flow cell 4 and, thus, external to the constrained-diffusion region where the liquid junction is formed. The external nature of the reservoir provides sufficient volume of liquid junction solution for a multiple use reference electrode without requiring a bulky storage unit for the junction solution at the constrained liquid junction itself to thereby facilitate provision of a miniaturized, modular construction, including an orientation independent, stable liquid junction as will be discussed in greater detail hereinafter. Throughout this disclosure, the term "stable liquid junction " shall be defined as a liquid junction capable of generating outputs that are constant from sample to sample within about 0.14 mV (millivolts).

Surprisingly, however, this location of the bulk of the volume of liquid junction solution remotely from constraint 18 did not generate the ion depletion problems commonly expected with conventional constrained diffusion junctions. This is particularly surprising in light of the reduced concentration of liquid junction solution utilized to facilitate sub-ambient storage, as will be discussed hereinafter. The reservoir may be designed in various sizes and shapes, depending upon the design of the overall analyzer system and the desired lifetime of the reference electrode assembly. For example, the reservoir could be formed by holding the junction solution in the typical tubing (or tubing with a bladder) leading to constraint 18 where the liquid junction is formed. Alternatively, the reservoir may be recognized as a separate container connected by tubing or other such means to the constrained-diffusion liquid junction. Appropriate separate structures that may be used as the reservoir include bottles or tanks and so on.

The liquid junction solution comprises an aqueous solution of a salt having equivalent cationic and anionic conductances, as are well known in the art and include equitransferent salts, such as KCl, $KNO_3$ and equivalents thereof Non-equitransferent salts, such as NaCl, NaBr, KBr, NaNO3 equivalents thereof and so on may also be used, however, these lead to increased liquid junction potentials. Preferred are equitransferent salts (KCl, $KNO_3$, and mixtures thereof). Because of cost and availability KCl is the most preferred salt. Other items may optionally be present in the liquid junction solution, including, for example, compatible surfactants, or ions.

The use of silver ions in the liquid junction solution is useful in the embodiments where the reference contact region is a silver based material. Preferably, the electrical contact region does not have a barrier membrane and the salt solution (preferably KCl) is non-saturated. In this situation, the present invention utilizes a junction solution further comprising $Ag^+$ ions, the ions preferably present in an amount sufficient to establish stable potentials at the silver based reference contact region but low enough so as to not induce fouling at the porous material constraint. It is known from the prior art that the concentration of $Ag^+$ ions present at saturation is dependent on the concentration of the electrolyte salt present in the junction solution (e.g., see Forbes, G. S., *Journal of the American Chemical Society*, 33, pp. 1937–46 (1911), hereby incorporated by reference). Preferably, the $Ag^+$ ions are included in the junction solution to the point of saturation when the KCl solution is used at a concentration of less than about 2 M. Preferably when the KCl is present in a concentration of greater than about 2 M to saturation (4.2 M at room temperature or 7.1 M at 100° C.), then the $Ag^+$ ions are provided in a concentration below saturation from about 0.01 mM to about 1 mM, most preferably 0.6 mM. The $Ag^+$ ions may be provided to the salt solution or formed in conjunction with the preparation of the junction solution by any number of familiar methods. For example, the junction solution may be prepared from a dilution of a saturated KCl/saturated AgCl solution;

addition of solid KCl to a 2 M KCl/saturated AgCl solution; dissolution of appropriate quantities of KCl and $AgNO_3$ in water, and so on.

Any desired concentration of the equitransferent salt in the junction solution may be utilized. Although saturated solutions of the salt may be used, one of the advantages of the inventive assembly is that the salt may be used in a concentration below saturation. In a preferred embodiment, a non-saturated solution of the salt is employed. Preferably KCl is selected as the salt and used in an amount ranging from about 0.5 M to about 7.1 M, more preferably 1 M to 4.5 M, and most preferably about 3.2 M. One of the advantages in using a non-saturated solution is particularly evident when a Ag/AgCl material is used as the reference contact region because with the non-saturated KCl solution, the $Ag^+$ concentration present at saturation is lowered (thus assisting in minimizing AgCl dissolution). Another advantage in using a non-saturated solution is to facilitate sub-ambient usage and/or storage since this eliminates the likelihood of KCl precipitation in the liquid junction flowpaths.

The means for moving the liquid junction solution from the reservoir to the constraint region may be selected from various known devices, taking into effect the overall design of the analyzer. Included in the definition of devices that may be selected for the means for actively moving the liquid are devices such as pumps, syringes, and the sort. For automated systems, a peristaltic pump 15, reciprocating syringe or other such device is particularly useful.

The design of the analyzer may be such that the device used for movement of the junction solution may also be used for moving other liquid(s) in the analyzer, such as, for example, the sample solution, calibration solution, wash solution, combinations thereof, and so on. Alternatively, a device specific to movement of the liquid junction solution alone may be used. The flow rate and volume of the liquid junction solution may be adjusted to the specifications of the analyzer to provide a concentration of electrolyte salt at the liquid junction that resembles that of the salt solution of the reservoir, as recognizable to those skilled in the art.

Reference contact region 13 may be placed anywhere within analyzer 1 as long as it may function so that electrical contact is made between the sensing equipment and the liquid junction solution. Suitable materials for the reference contact region are materials including conductive metals, alloys thereof, and composites thereof having acceptable conductive properties, as are easily recognized by those skilled in the art (i.e. materials that are capable of providing an electrochemically reversible redox electrode couple). Particularly suitable are silver based materials and calomel ($Hg/Hg_2Cl_2$). More preferably, silver based materials are used (e.g., $Ag/Ag^+$ and $Ag/AgCl$). Although barrier membranes covering all or a portion of the electrical contact regions may be used, for ease of use and to facilitate miniaturization, preferably no such barrier membrane is present in reference electrode 5. Ability of the present invention to operate successfully without such a barrier membrane, without excessive fouling of constraint 18 was surprising in light of the teachings of the prior art. In this regard, various configurations of reference electrode 5 were tested and shown to operate successfully without substantial degradation of constraint performance over a uselife of at least 28 days.

For ease of use, reference contact region 13 may be designed into multiple conductive regions that are connected together to facilitate electrical contact between the sensing equipment and the liquid junction. For example, two regions may be used. In this design, a first region 11 is where the contact is made with the liquid junction solution, with the first region prepared from materials that are capable of providing an electrochemically reversible redox electrode couple. Second region 25 is directly connected to the first region but does not necessarily touch the liquid junction and may be prepared using any suitable electrically conductive materials (i.e. extending beyond those materials capable of providing an electrochemically reversible redox electrode couple). In this design, the function of the second region is to facilitate making electrical contact to the sensing equipment. Illustrative of this set up would be a first region 11 comprising a conductive wire connected to the liquid junction solution and a second region 25 that is a "pad" embedded or screen printed onto the non-conductive flow cell 4 as shown. In this embodiment the wire would be set into the pad in a perpendicular fashion. The electrical contact(s) from the sensing equipment would touch the second region pad, thus providing indirect contact between the sensing equipment and the liquid junction solution.

The reference electrode assembly may be used in conjunction with one or more potentiometric indicator or working electrode(s) 6 whose response depends upon analyte concentration. Ion-selective electrodes based on solvent polymeric membranes are examples of such working electrodes. Examples of analytes that may be measured include, for example, chloride, potassium, calcium, sodium, pH, bicarbonate, magnesium, and so on. Reference electrode 5 and a working electrode 6 constitute individual galvanic half-cells which together comprise an electrochemical cell which allows for potentiometric quantitative analysis. The reference electrode assembly is capable of providing a steady and stable potential sufficient for potentiometric analysis over the clinically relevant range of ionic strengths, protein concentrations, and hematacrit levels. Optionally, the reference electrode assembly may be packaged together with mini-integrated working electrodes 6 stationed on a sensor module 9 such that the entire configuration is a single disposable unit.

It is to be understood that various modifications to the invention will be apparent to and can readily be made by those skilled in the art, given the disclosure herein, without departing from the scope and materials of this invention. It is noted that the following examples given herein are intended to illustrate and not to limit the invention thereto.

EXAMPLES

Figure 1:
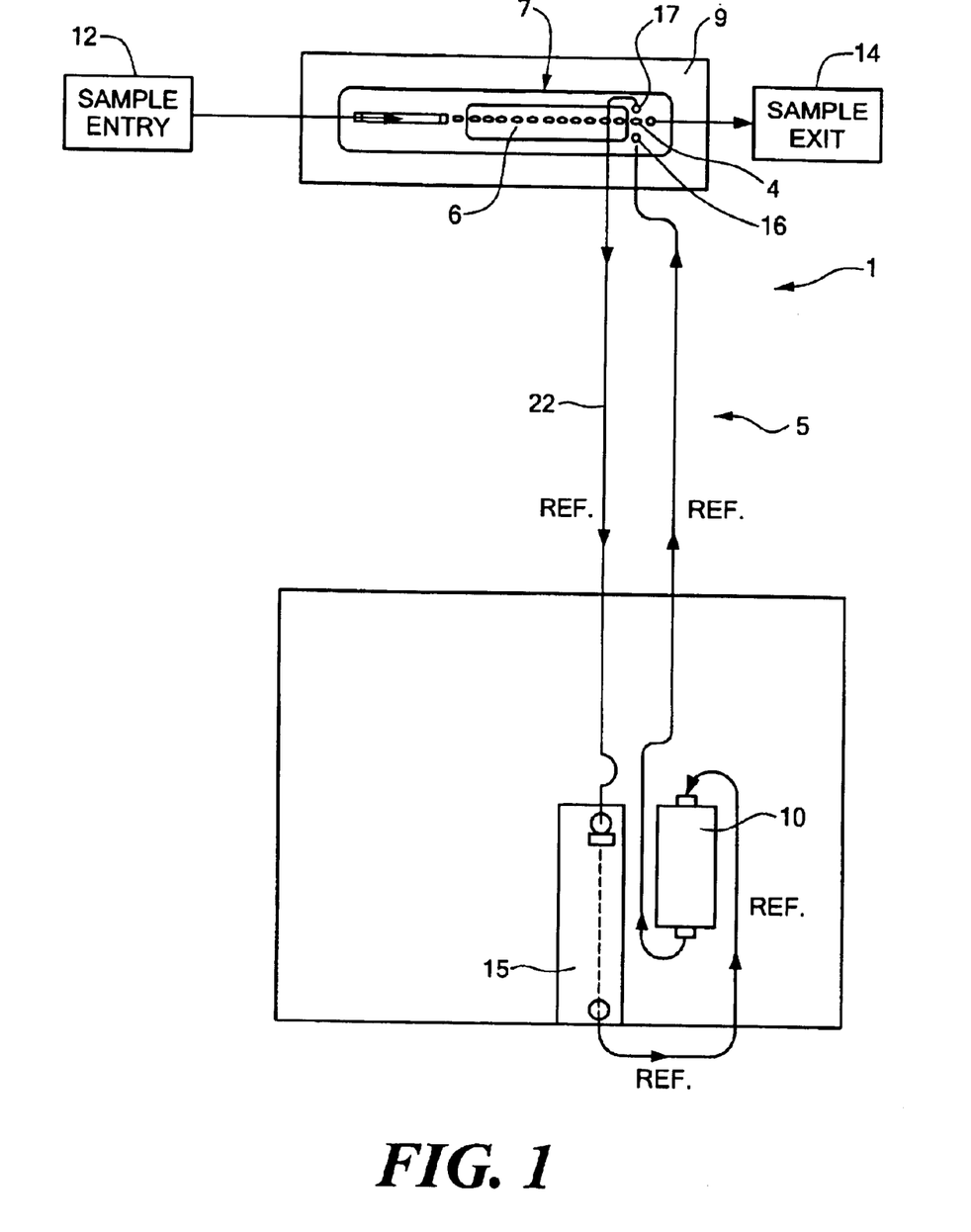
FIG. 1 is a schematic view of an embodiment of a reference electrode assembly of the subject invention.
Figure 2:
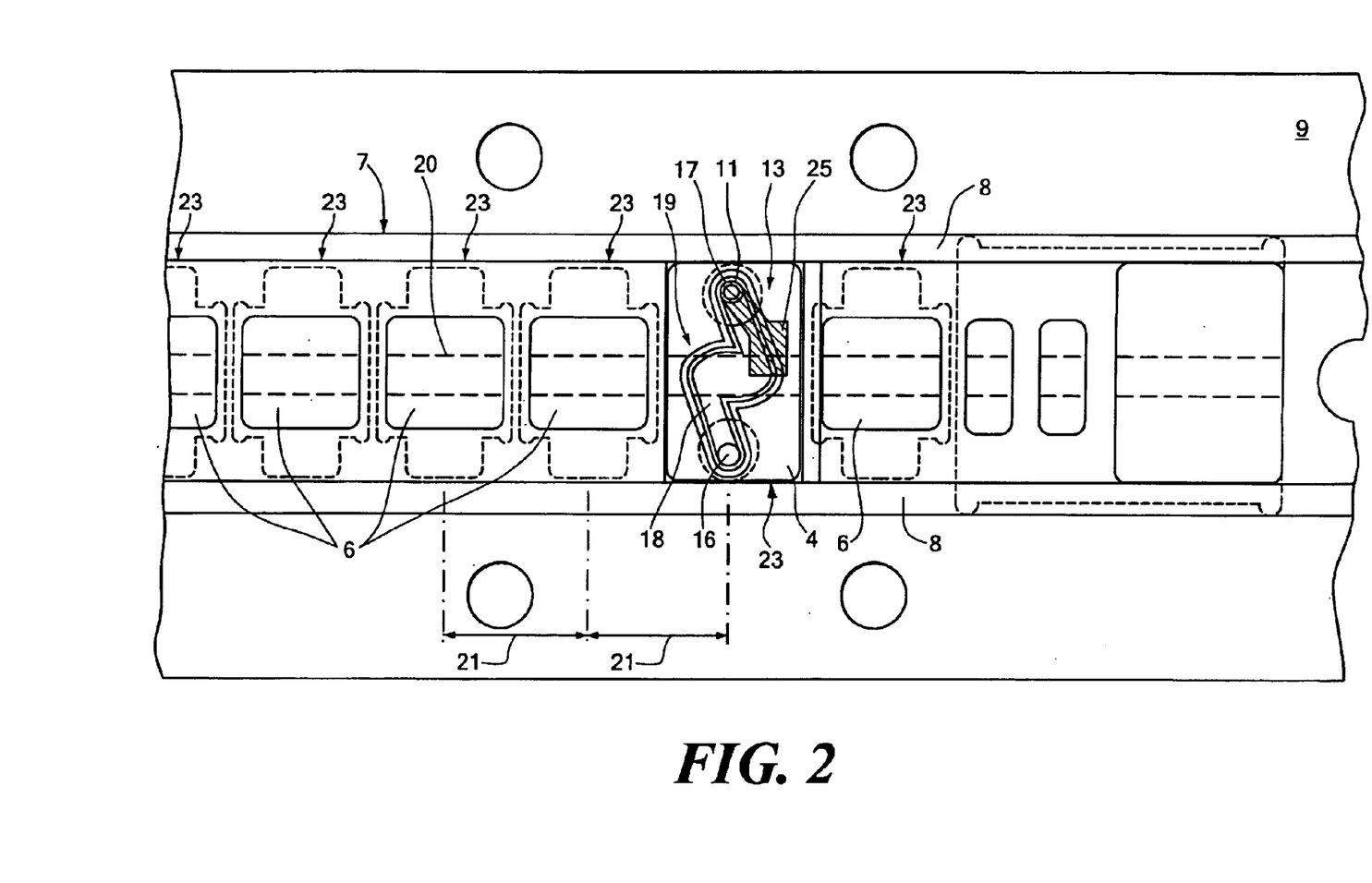
FIG. 2 is a plan view of a portion of an array of working electrodes, including a flow cell of the reference electrode of FIG. 1.

Many configurations of reference electrode 5 may be designed. FIGS. 1–2 illustrate a configuration of a reference electrode assembly incorporated into a mini-integrated electrochemical analyzer 1 where the reference electrode has a lifetime of at least about one month with typical clinical usage.

More particularly, in FIG. 1 the schematic view illustrates a flow cell 4 of a reference electrode 5 positioned serially within an array 7 of a plurality of working electrodes 6. The electrodes are each disposed between a pair of guide rails 8 of a sensor module 9. The junction solution is pumped from a remote external reservoir 10 located apart from the liquid junction region of the reference electrode 5. The orientation of the reservoir 10 is not gravity specific, and thus the reservoir may be placed anywhere that is convenient to the other items of the analyzer. From the sample entry 12 portion of the sensor array, the analyte containing sample is pumped along sample solution flow path 20 through the sample chambers of various working electrodes 6 and through sample chamber 19 of flow cell 4 to a sample exit 14. Sample solution flow path 20 and liquid junction solution flow path 22 are separate paths. A common pump 15 is used for sample solution movement and junction solution movement. The junction solution is moved along liquid junction solution flow path 22 from the remote reservoir 10 to flow cell 4 of the reference electrode 5 each time a sample is run. The movement of the junction solution may be continuous but more preferably occurs only at such time as when a sample (or reference liquid such as a calibrator or quality control material) is present. Once used, the junction solution may be discarded as waste or flow path 22 may be configured as shown to enable the junction solution to be recycled and pumped back to reservoir 10. Preferably the solution is recycled, thus extending the lifetime of the reference electrode and also eliminating waste. In a particularly preferred configuration, the liquid junction solution is re-circulated and pumped with the introduction of each analyte sample and becomes stagnant after the testing of the sample is completed. Preferably, only a small volume of the reference electrolyte solution is moved to flow cell 4 of the reference electrode 5 and optionally recycled back to the external reservoir 10 per cycle, in conjunction with a small front-end or flow cell reference electrode assembly particularly useful in a mini-integrated analyzer.

As shown in FIGS. 1 and 2, the liquid junction solution may be pumped from the reservoir 10 to an inlet tube 16 over the region of porous material forming constraint 18. The porous material (preferably a permeable membrane) is attached to flow cell 4 by fastening a gasket over the material whereby a hermetic seal between the porous material and the flow cell is formed. The area constrained by the porous material is where the sample and the junction solution interface in the flow cell thus forming the liquid junction. The flow cell has a rounded elliptical, or preferably circular shaped sample chamber 19, these shapes of the chamber being helpful in providing an effective washout of the entire chamber and also to minimize bubble trapping. Junction solution depletion occurs at a rapid rate once the junction solution is held stagnant in the flow cell. Design of the surface areas and volume of chamber 19 relative to the sample volume and hold time may be manipulated to provide the desired performance. Preferably when such an elliptical shaped chamber is used, the constraint region is attached thereto. Advantageously, unlike many open junctions discussed hereinabove which are typically geometry dependent, the liquid junction formed by constraint 18 of the present invention is adapted for use with such elliptical or other non-circular shaped chambers. In a preferred embodiment, chamber 19 has a volume of from about 0.5 to about 17 $\mu$L, most preferably, a circular chamber has a volume of about 0.5 $\mu$L. As discussed hereinabove, electrical contact region 13 has two parts. The first region 11 is a Ag° or Ag/AgCl wire that is imbedded in a second contact region 25 that is attached to the non-conductive flow cell. The second region 25 has an exposed portion in the flow cell through which the electrical contact is made with the sensing equipment. The sample is removed from the sensor array through the sample exit 14 as waste while the junction solution is recycled back to the reservoir 10 via the exit tube 17.

In the embodiment shown in FIGS. 1 and 2, the reference electrode most preferably employs a non-saturated KCl liquid junction solution stored in a reservoir having a volume of from about 1 mL to about 50 mL (most preferably 8 mL), a membrane porous constraint region, and a silver based reference contact region without a barrier type of membrane. Advantages of this embodiment include a multiple-use capability, with minimum fouling of the porous material region over the use lifetime. The assembly may be stored as a dry reference electrode assembly. The KCl junction solution may be released form the reservoir which then easily wets the flow cell upon first use, where bubble formation at the membrane region (which typically accompanies a first use) is reduced. Also, in this preferred embodiment, the junction solution is re-circulated and thereby greatly minimizes the reservoir volume necessary for multiple use and also reduces the amount of waste generated as compared to systems with one-use only solutions. This reference electrode also may be stored at subambient temperatures with a reduced possibility of salt crystallization while providing reproducible results having an acceptable accuracy with multiple testing capability. In this embodiment there is exhibited an adequate ionic strength independence at relatively low junction solution concentration, as low as about 0.5 M KCl. This is unexpected based on the Henderson equation for the liquid junction potential of two freely diffusing liquids.

As best shown in FIG. 2, flow cell 4 is modular to facilitate disposition serially with electrodes 6 at substantially any convenient electrode receiving location 23 along flow path 20 of sensor module 9. Once a convenient location is determined, analyzer 1, including the electronic portion thereof, may be configured accordingly in a manner familiar to those skilled in the art. In a preferred embodiment as show, flow cell 4 has nominally the same, relatively miniaturized footprint or dimensions as each working electrode 6 and thus may be interchangeably placed in any of the electrode receiving locations 23. As used herein, the term "footprint" shall be defined as a maximum dimension in at least two orthogonal dimensions. As shown, flow cell 4 fits within guide rails 8 in nominally the same manner and occupies the same dimension 21 in the direction of flow path 20 as each electrode 6. In a preferred embodiment, this sample flow path dimension 21 is approximately 0.5 cm center to center as shown. In addition to permitting such locational flexibility, this miniaturization advantageously enables determination of analyte content using a relatively small sample. For example, the present invention enables a sample as small as 53 $\mu$L to completely fill sample path 20 within a complement of 13 working electrodes 6 plus flow cell 4 for analyte determination.

This uniformity or modularity also advantageously facilitates use of standardized componentry in analyzer 1, such as, for example, use of a single pair of guide rails 8 in sensor module 9 to secure both working electrodes 6 and flow cell 4. An important additional aspect of this modularity, as provided in part by use of remote reservoir 10, the configuration of flow cell 4 and use of constraint 18, is the ability of flow cell 4 to be physically located either upstream or downstream along sample flow path 20, of one or more working electrodes 6. Thus, working electrodes 6 may be disposed within sensor module 9 on opposite sides of flow cell 4 as shown. This aspect advantageously provides flexibility of design and use of analyzer 1. This flexibility may be useful in enabling a single analyzer design to accommodate various numbers of working electrodes. For example, guide rails 8 may be shortened or provided with blanks on either side of flow cell 4 in the event relatively few working electrodes 6 are desired, or alternatively, may be lengthened to accommodate additional electrodes to analyze additional analytes.

Since both flow cell 4 and working electrodes 6 are orientation independent, the entire array 7 may be operated at substantially any orientation. This aspect advantageously facilitates use of the present invention in numerous mobile applications where it may be inconvenient to maintain the array in a level orientation. This feature also serves to provide additional flexibility in analyzer design by, for example, enabling constraint 18 and accordingly, inlet tube 16 and exit tube 17 to be disposed either above, below or alongside sample flow path 20. A still further advantage of the configuration of the present invention is that the miniaturized modular design of sensor module 9 including flow cell 4 may be sufficiently simple and inexpensive to produce that it may be conveniently disposed and/or recycled at the end of its useful life and replaced with a new or refurbished module.

Example 1

Reference flow cells were either machined from rigid acrylic or injection molded using ABS plastic. For each flow cell constructed, the constraint material was an ion and water permeable free-standing 0.001" thick cellophane (uncoated regenerated cellulose) film membrane obtained from Flexel, Inc., Atlanta, Ga. The film was placed over an elliptical shaped chamber 19 of the flow cell (the chamber having a volume of approximately 3.5 $\mu$L). The film was hermetically sealed to the chamber region of the flow cell with compression from a gasket on top of the flow injection sensor module assembly. Sample solution and liquid junction solution flowed past each other on opposites sides of the surface of the cellophane film membrane at a flow rates of from about 5 to about 100 $\mu$L/sec. A common peristaltic pump was used to simultaneously move both solutions. Electrical contact was established via an electrochemically plated 0.012" Ag/AgCl or Ag wire located either within the remote reservoir solution or in the base of the flow cell imbedded in screen printed epoxy silver in a perpendicular fashion to extend into the inlet tube of the flow cell. The sensing equipment used was a HP 3457A digital multimeter. The total volume of the solution in the junction reservoir ranged from approx. 8 mL to approx. 15 mL. The junction solution was moved from the remote reservoir to the flow cell and past one surface of the cellophane membrane with every sample solution. The junction solution was then either re-circulated back to the reservoir or sent to waste after the measurement cycle. Electrode measurements were taken when both the sample and liquid junction solutions were stationary.

Various junction solutions were tested. The aqueous based solutions tested were (a) 1.5 M of KCl saturated with AgCl (approx. 0.25 mM); (b) 2.0 M of KCl saturated with AgCl (approx. 0.6 mM); (c) 3.5 M of KCl with 0.6 mM of AgCl; and (d) 4.0 M of KCl with 0.6 mM of KCl, where some of the solutions further comprised about 0.05 g/L of BRIG® 700 (manufactured by ICI Surfactants, Wilmington, Del.). The wet up of a fully dry system was established to commercially desirable specifications in less than five minutes. Ionic strength dependence over a clinically significant range of 0.120 mM to 0.200 mM was evaluated. Reference potential changes of less than 0.5 mV were measured for all solutions tested over a time period averaging approx. 1 month. This reference electrode was used together with separate planar ion-selective electrodes sensitive for pH, potassium, ionized calcium, and sodium for the analysis of these analytes.

Example 2

Reference electrodes were prepared as described in Example 1 with the following exceptions.

The placement of the reference contact region (a Ag wire) was varied. A three dimensional sodium ISE working electrode (200 Series obtained from Ciba Corning Diagnostics Corp., Medfield, Mass.) was tested with three reference electrodes using a junction solution of 2 M KCl/saturated with AgCl. The reference electrode used as the control was a 200 Series Corning Diagnostics Corp. three-dimensional type of reference electrode. The calibration reagents were that used on the Ciba Corning Diagnostics Corp. 644 Instrument.

In Set A, the reference electrodes tested had a Ag wire located in the base inside the chamber. A reference electrode prepared with a Ag wire in the base of the flow cell was tested over a period of 35 minutes. The average within sample drift was −0.047 mV/sec. A reference electrode with a Ag wire in the remote reservoir was tested under the same conditions and was found to have an average within sample drift of −0.001 mV/sec. The control 200 Series reference electrode had an average within sample drift of −0.0004 mV/sec.

In Set B, the reference electrodes tested had a Ag wire located in a base outside the chamber. A reference electrode prepared with a Ag wire in the base outside the chamber of the flow cell was tested over a period of 35 minutes. The average within sample drift was 0.001 mV/sec. A reference electrode with a Ag wire in the remote reservoir was tested under the same conditions and was found to have an average within sample drift of 0.0004 mV/sec. The control 200 Series reference electrode had an average within sample drift of 0.001 mV/sec.

Example 3

Reference electrodes were prepared as described in Example 1 with the exception that the chamber had a larger volume (16.8 μl) as compared with the chamber of Example 1 (which had a volume of 3.5 μl). A three dimensional sodium ISE working electrode (as described in Ex. 2) was tested with three reference electrodes using a junction solution of 2 M KCl/saturated with AgCl. The reference electrode used as the control was a 200 Series Corning Diagnostics Corp. three-dimensional type of reference electrode. The calibration reagents were that used on the Ciba Corning Diagnostics Corp. 644 Instrument. The reference electrodes tested had a Ag wire located in a base inside the chamber. The electrodes were tested over a period of 35 minutes. The average within the sample drift was −0.012 mV/sec. When repeated the average within the sample drift was −0.028 mV/sec. The control 200 Series reference electrode had an average within sample drift of 0.001 mV/sec.

That which is claimed is:

1. A method of providing a reference signal in a system for potentiometric quantitative analysis, said method comprising the steps of:

(a) providing a flow cell in any of a plurality of electrode receiving positions on a sensor support member of said system, each of said electrode receiving positions adapted to support one of a plurality of working electrodes or said flow cell, wherein said flow cell is adapted to be serially retained within a sample flow path of the system;

(b) interfitting said flow cell in series with ones of said plurality of working electrodes within said plurality of electrode receiving positions;

(c) storing a liquid junction solution in a remote reservoir connected to said flow cell for delivery of said liquid junction solution to said flow cell and for receipt of said liquid junction solution therefrom;

(d) moving a sample solution through said sample flow path to said flow cell to form a liquid junction between the sample solution and said liquid junction solution about a porous constraint whereby said sample solution is disposed in contact with one side of said porous constraint, said constraint being adapted to substantially prevent bulk flow of said liquid junction solution therethrough; and (e) circulating said liquid junction solution, comprising a non-saturated equitransferent salt, in conjunction with said step of moving said sample solution, whereby a volume of said liquid junction solution is pumped from said remote reservoir towards said flow cell and from said flow cell towards said reservoir, whereby said liquid junction solution is disposed in contact with an other side of said porous constraint and whereby said liquid junction solution is electrically connectable to sensing equipment by a reference contact region in physical contact with said liquid junction solution, said reference contact region providing said reference signal, wherein said reference contact region is a silver based conductive material and said junction solution comprises (a) KCl present in an amount of about 3.2 M and (b) $Ag^+$ ions present in an amount of about 0.6 mM.

* * * * *

UNITED STATES PATENT AND TRADEMARK OFFICE
CERTIFICATE OF CORRECTION

PATENT NO. : 6,719,888 B1
DATED : April 13, 2004
INVENTOR(S) : Andy D. C. Chan et al.

It is certified that error appears in the above-identified patent and that said Letters Patent is hereby corrected as shown below:

Column 3,
Line 12, "shortcoming" should read -- shortcomings --; and

Column 4,
Line 51, "1" should read -- 5 --.

Signed and Sealed this

Eighteenth Day of October, 2005

JON W. DUDAS
*Director of the United States Patent and Trademark Office*